United States Patent [19]

Schiller

[11] 4,127,858
[45] Nov. 28, 1978

[54] DEVICE FOR SUPPLYING AN IMPRINTING APPARATUS WITH A RECORDING TAPE MEANS

[76] Inventor: Alfred E. Schiller, Landhausweg 4e, Baar, Switzerland

[21] Appl. No.: 801,815

[22] Filed: May 31, 1977

[30] Foreign Application Priority Data

Jun. 4, 1976 [DE] Fed. Rep. of Germany ....... 2625325

[51] Int. Cl.² .......................................... G01D 15/24
[52] U.S. Cl. .................................... 346/136; 346/145
[58] Field of Search .................. 346/136, 145, 33 ME; 128/2.06 G

[56] References Cited

U.S. PATENT DOCUMENTS

| | | | |
|---|---|---|---|
| 2,718,450 | 9/1955 | Leonard et al. | 346/145 UX |
| 3,082,970 | 3/1963 | Rasmussen | 346/33 ME |
| 3,864,694 | 2/1975 | Tamura | 346/136 |

FOREIGN PATENT DOCUMENTS 7,324,683 11/1973 Fed. Rep. of Germany.
7,424,516 5/1974 Fed. Rep. of Germany.

*Primary Examiner*—George H. Miller, Jr.
*Attorney, Agent, or Firm*—O'Brien and Marks

[57] ABSTRACT

A device for supplying an imprinting apparatus with a recording tape means, the device having a container means for storage of said recording tape means and movable between an operating position and a refilling position, the device including a driving roll and a non-driven pressure exerting roll, whereby the two rolls define a clamping gap therebetween and form a passage for said recording tape means. The device is characterized in that one of said two rolls is arranged at the front end of said container means, such that said clamping gap is formed only if said container means is located in its operating position.

13 Claims, 9 Drawing Figures

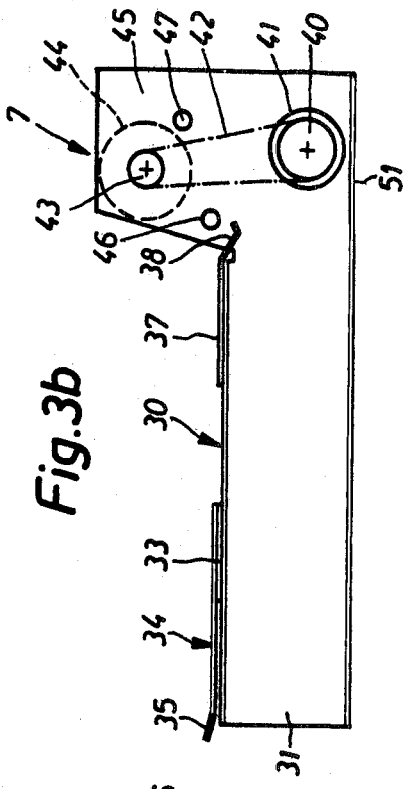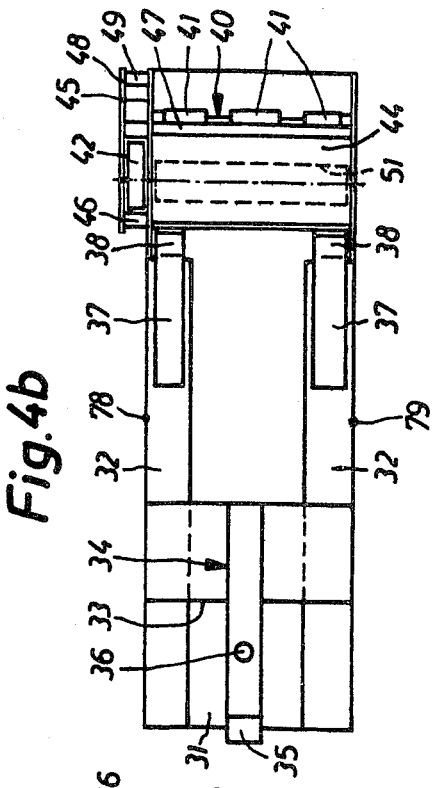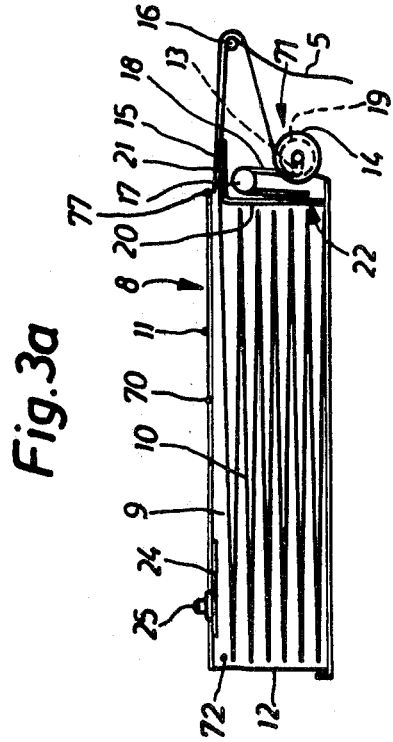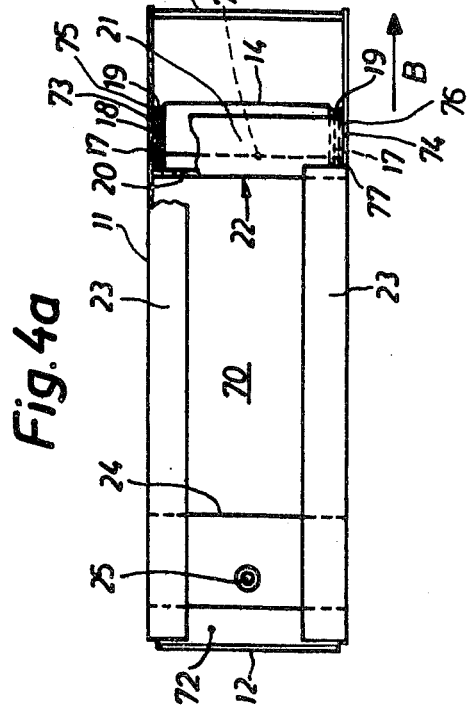

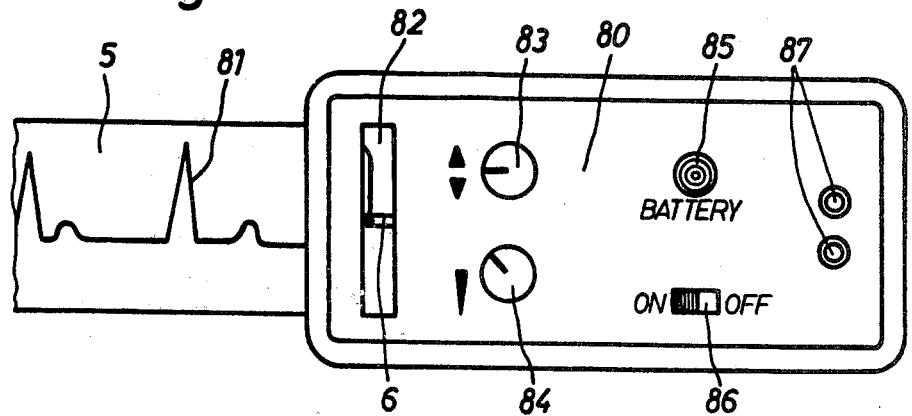
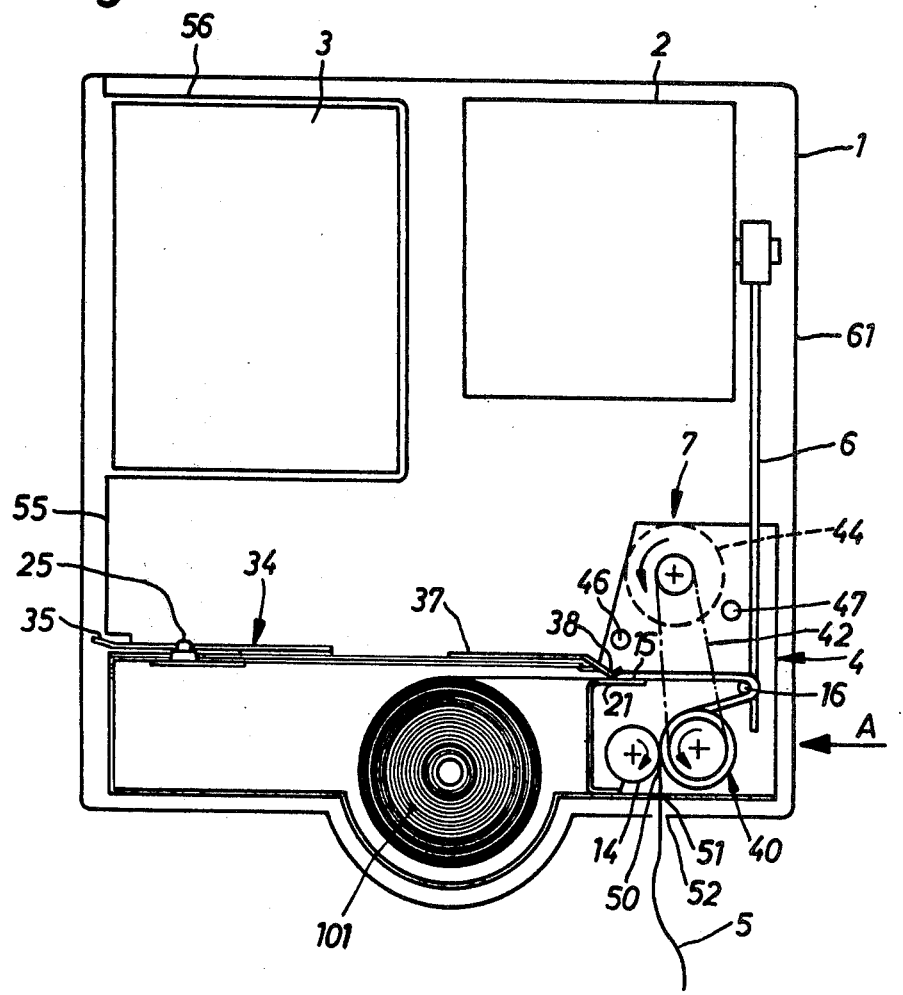

DEVICE FOR SUPPLYING AN IMPRINTING APPARATUS WITH A RECORDING TAPE MEANS

BACKGROUND OF THE INVENTION

1. Field of the Invention

The present invention relates to a device for supplying an imprinting apparatus with a recording tape means, said device including a storage space for said recording tape means arranged in a container means for storage of said recording tape means, whereby said container means is movable between an operating position and an easily accessible refilling position and arranged for receival and storage of said recording tape means in an accumulated, condensed form, said device including further a driving roll and a non-driven pressure exerting roll, said two rolls defining a clamping gap therebetween and forming a passage for said recording tape means.

2. Description of the Prior Art

It is generally known that imprinting apparatuses, specifically in electrocardiographs, including a recording stylus driven by a galvanometer which detects the currents of the heart are provided with a paper tape supply stored in form of a roll. For use, such paper roll is to be inserted into a storage space provided within the printing apparatus. When exhausted, the paper roll will be removed or extracted, respectively, out of such storage space and a new paper roll inserted therein. Such an arrangement including a paper roll requires a rather large space within the imprinting apparatus and has hitherto prevented a design of an imprinting apparatus, specifically of an electrocardiograph, which is small enough to be easily portable and especially easily manageable.

SUMMARY OF THE INVENTION

Hence, it is a general object of the present invention to provide a device for supplying an imprinting apparatus with a recording tape means which affords little space requirements and is easily manageable.

It is a further object to provide a device for supplying an imprinting apparatus with a recording tape means, said device comprising a storage space for said recording tape means arranged in a container means for storage of said recording tape means, whereby said container means is movable between an operating position and an easily accessible refilling position and arranged for receival and storage of said recording tape means in an accumulated, condensed form, said device comprising further a driving roll and a non-driven pressure exerting roll, said two rolls defining a clamping gap therebetween and forming a passage for said recording tape means which is characterized in that one of said two rolls is arranged at the front end of said container means, which end faces said imprinting apparatus, such that said clamping gap is formed only if said container means is located in its operating position, and in that the non-driven pressure roll is supported by said container means of said tape means.

It is a further object to provide a device in which said recording tape means is stored in said container means in a folded, pleated form.

A further object is to provide a device in which said recording tape means is stored in said container means in a rolled form.

It is still a further object to provide a device wherein said container means features the form of a cassette which is insertable into said imprinting apparatus as well as retractable from said imprinting apparatus and arranged to be completely removable therefrom.

Yet a further object is to provide a device comprising further a guide roll arranged within said cassette, which guide roll deflects the leading portion of said recording tape means prior to its entry into said clamping gap.

It is a further object to provide a device wherein said guide roll is substantially in alignment with the tape portion drawn off from the accumulated stored tape means and said pressure roll is arranged beyond said guide roll and offset therefrom such as to produce a deflection of the drawn off tape portion prior to its entry into the clamping gap in an amount exceeding 90°.

A further object is to provide a device comprising further a spring means biassing said pressure roll in a direction towards said clamping gap.

A further object is to provide a device wherein said imprinting apparatus is provided with a receiving means for said cassette, said receiving means having a C-shaped cross section and being arranged within said imprinting apparatus, said receiving means serving as support for said driving roll and its driving means and simultaneously forming a guiding means for said cassette.

A further object is to provide a device wherein said cassette and said its receiving means are provided each with a portion of a locking means, said portions being engaged when said cassette is in its operating position.

Yet a further object is to provide a device wherein said receiving means is provided with at least one leaf spring means for holding down the recording tape means section to be inserted against a guide surface provided at the cassette.

A further object is to provide in combination with an electrocardiograph for producing an electrocardiogram, comprising a recording stylus and a galvanometer for driving said stylus, which galvanometer detects the currents of a heart, a device for supplying an imprinting apparatus with a recording tape means, said device comprising a storage space for said recording tape means arranged in a container means for storage of said recording tape means, whereby said container means is movable between an operating position and an easily accessible refilling position and arranged for receival and storage of said recording tape means in an accumulated, condensed form, said device comprising further a driving roll and a non-driven pressure exerting roll, said two rolls defining a clamping gap therebetween and forming a passage for said recording tape means, characterized in that one of said two rolls is arranged at the front end of said container means, which end faces said imprinting apparatus, such that said clamping gap is formed only if said container means is located in its operating position, and in that the non-driven pressure roll is supported by said container means of said tape means, and whereby said container means features the form of a cassette which is insertable into said imprinting apparatus and arranged to be completely removable therefrom.

BRIEF DESCRIPTION OF THE DRAWINGS

The present invention will be more fully understood by reference to the following detailed description thereof when read in conjunction with the attached drawings, and wherein:

FIGS. 3a and 3b are sectional views of a cassette in accordance with the invention and of the container of the cassette, which container is mounted within the electrocardiograph, whereby the cassette is shown in its withdrawn position, FIGS. 4a and 4b are top views of the parts of the device shown in FIGS. 3a and 3b, FIG. 6 is a view of the complete electrocardiograph in direction of the arrow C of FIG. 1, and FIG. 7 is a view similar to the view of FIG. 1 of an embodiment having the tape supply in a spirally rolled form.

DETAILED DESCRIPTION OF THE PREFERRED EMBODIMENT

Figure 1:
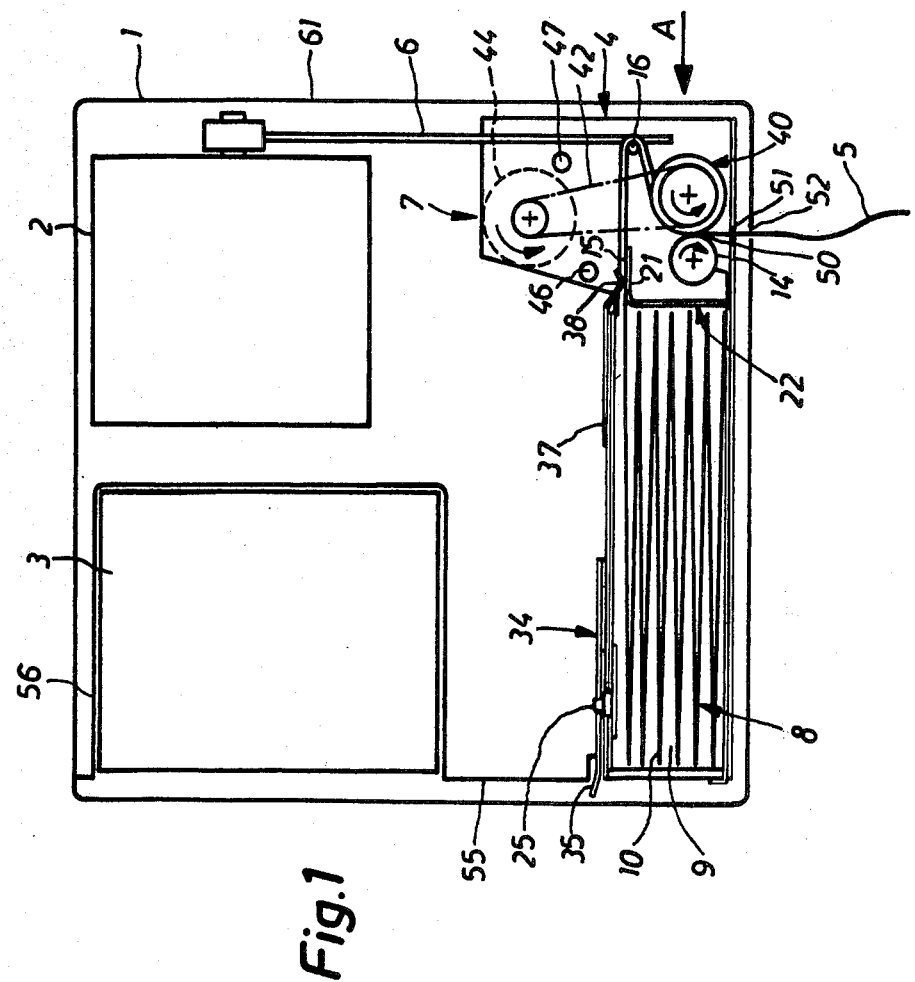
FIG. 1 is a schematical cross-sectional view of an electrocardiograph featuring the device of the invention.

The electrocardiograph shown in FIG. 1 of the drawings comprises a casing 1 in which there is mounted a galvanometer 2 which detects the performance of the muscles of the heart and comprises furthermore a replaceable battery, or energizer unit 3. The galvanometer is governed by a not-shown electronic circuit. These members are well known in the art and thus a special description thereof is omitted. In said casing 1 there is furthermore arranged a device shown generally at 4, which device supplies an endless recording paper tape 5 or paper web 5, respectively. In the preferred embodiment this paper tape 5 comprises a heat sensitive paper which is imprintable by means of a heatable stylus 6. This stylus 6 is driven by the galvanometer 2. Such apparatus is readily available in the market.

Figure 2:
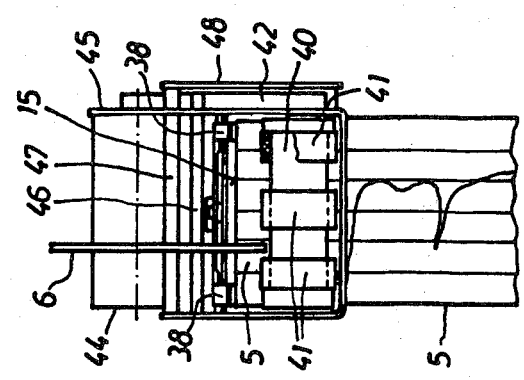
FIG. 2 is a view of the device of FIG. 1 seen in the direction of the arrow A, whereby the parts belonging to the electrocardiograph are omitted.

The device 4 intended for supplying the paper tape 5 to the electrocardiograph, and shown more in detail in FIG. 2 comprises two main portions, namely a container means 7 rigidly connected to the casing 1 and a cassette 8. The container means 7 (FIGS. 3b and 4b) guides the cassette 8, which cassette 8 can be inserted or slid in, respectively, into said container 7 and is retractable therefrom and can be completely removed from the container 7. Said two structural portions 7 and 8 are shown in FIGS. 1 and 2 in their operating position, in which the cassette 8 is inserted into the container 7, and in FIGS. 3 and 4 they are shown in the pulled out position of the cassette 8, in which position the cassette 8 is completely separated from the container 7 whereby its storage space 9 can be now refilled with a stack 10 of a multiply folded paper tape.

The cassette 8 comprises a casing 11 formed or bent, respectively, out of sheet metal, which casing 11 is open at its top 70 as well as at its front end 71 and at its rear end 72. At the rear end 72 there is thus provided a rear opening 12 through which a new supply of a stack of folded paper tape 10 can be inserted into the cassette 8. At the front end 71 of the cassette 8 there are supported two rolls, namely a pressure roll 14 carried at its ends in longitudinal slots 13 (FIG. 3a) extending in the longitudinal direction of the casing 11 and a guide roll 16 arranged about in or somewhat below the plane 15 defined by the leading portion of the paper tape extending out of the cassette 8, which guide roll 16 is mounted forward of the pressure roll 14 as seen in FIG. 3a. The pressure roll 14 is biased against the forward end (in FIGS. 3a and 4a the right hand end) of the longitudinal slots 13. To this end there are provided two torsional spring elements 18 which are connected at point 17 to the side walls 73 and 74, respectively, of the casing 11, which spring elements 18 engage grooves 19 provided in grooved discs 75, 76 provided at both ends of the pressure roll 14. The torsional spring elements 18 bear with their rear ends against a leg 20 of an angular element 22, the other leg 21 of which defining with its top surface the draw off plane 15 of the web-like paper tape 5. At its top side the cassette 11 is provided with two inwardly and against each other facing legs 23, extending from a point 77 located behind the pressure roll 14 until to the rear opening 12. These legs 23 are connected at the rear zone of the cassette by means of a laterally extending strap 24. This laterally extending strap 24 carries a locking pin 25.

The container 7 for receival of the cassette 8 is also provided with a housing 30 formed and bent of sheet metal and open at its front and rear end. The rear opening 31 of this casing 30 is dimensioned such that the cassette 8 can be slid into this casing 30 in the direction of the arrow B as shown in FIG. 4a. The inner surfaces of the side walls 78, 79 of the casing 30 act as guide elements for the casing 11 of the cassette 8. The casing 30 is provided at its upper side with two inwardly extending legs 32 which face each other and which are connected by means of a strap 33. A leaf spring 34 is mounted onto the strap 33, the free end of said leaf spring being bent upwardly. At its resilient portion forward of its free end 35 the leaf spring 34 is provided with a through hole 36 for suitable receipt of the locking pin 25.

To both front ends of the legs 32 is connected each to further leaf springs 37, the free end 38 of which is extending forwardly and being bent downwardly. Accordingly they extend into the path of travel of the leg 21 of the angular element 22 of the casing 11 of the cartridge 8 and depress the paper web 5, when the cassette 8 is in its inserted position inside the casing 30 against said leg 21 (FIG. 1). In the forward end of the casing 30 and close to its bottom there is mounted a driving roll 40, onto which there are mounted three spaced rubber rings 41. At its upper end as seen in FIG. 4b the driving roll 40 carries a not-shown gear wheel drivingly connected with a toothed belt 42. This toothed belt 42 is on its side driven by a toothed gear wheel 43 mounted on the driving shaft of a micro DC-motor 44 known as such. This DC-motor is mounted in an overhung position to an upwardly elongated supporting plate 45 at one side of the casing 30. This supporting plate 45 itself is supported by the adjacent wall of the casing 30 by means of columns 46, 47. These columns support furthermore a covering plate 48 encasing to a large extent the toothed belt 42. The covering plate 48 is additionally mounted to a short column 49 carried by the wall 45.

The dimensions of the cassette 8 and of the container 7 are chosen such that the cassette 8 fits slidingly with little play in the container 7. In the fully inserted position of the cassette 8 the rolls 14 and 40 abut each other under the pressure exerted by the torsional springs 18 and define together a clamping gap 50, through which the paper tape 5 driven by the driving roll 14 and the in the opposite direction rotating and following pressure roll 14, after said paper tape 5 has passed the guide roll 16, is being pulled. Thereafter the paper tape 5 exits the housing 30 through a slit 51 and exits the housing 1 through a slit 52 located below slit 51 (FIG. 1). Out of FIGS. 3 and 4 it can be specifically seen, that after a new paper stack 10 of a folded over paper web has been inserted through the opening 12 into the storage space 9 of the cassette 8, and after the leading section of the paper web has been bent around or folded back, respectively, around the guide roll 16, and after a certain length of the web has been withdrawn from the stack, the threading of the paper web 5 into the clamping gap 50 is achieved automatically by itself in that when the cassette 8 has been fully inserted into the container 7 and thus in its end position, the hanging down leading portion of the paper web comes to lay upon the driving roll 40 and will be pressed by means of the pressure roll 14 being moved towards the paper web against the circumference of the driving roll 40. If now the motor 44 gets energized, the paper web automatically is fed towards the slit 51 through said slit 51 as well as through the slit 52. The threading is thus automatically carried out without any further measure and exclusively due to the feature, that the rolls 14, 40 defining the clamping gap 50 are separately located in structural members 7, 8 which must be removed from each other in order to insert a fresh paper stack.

The micro DC-motor is supplied with electric power from the batteries of the battery unit 3 via an electronic speed regulator of known design and thus not further described. In order to exchange used batteries the battery unit 3 can be removed out of the casing 1 of the electrocardiograph.

Figure 5:
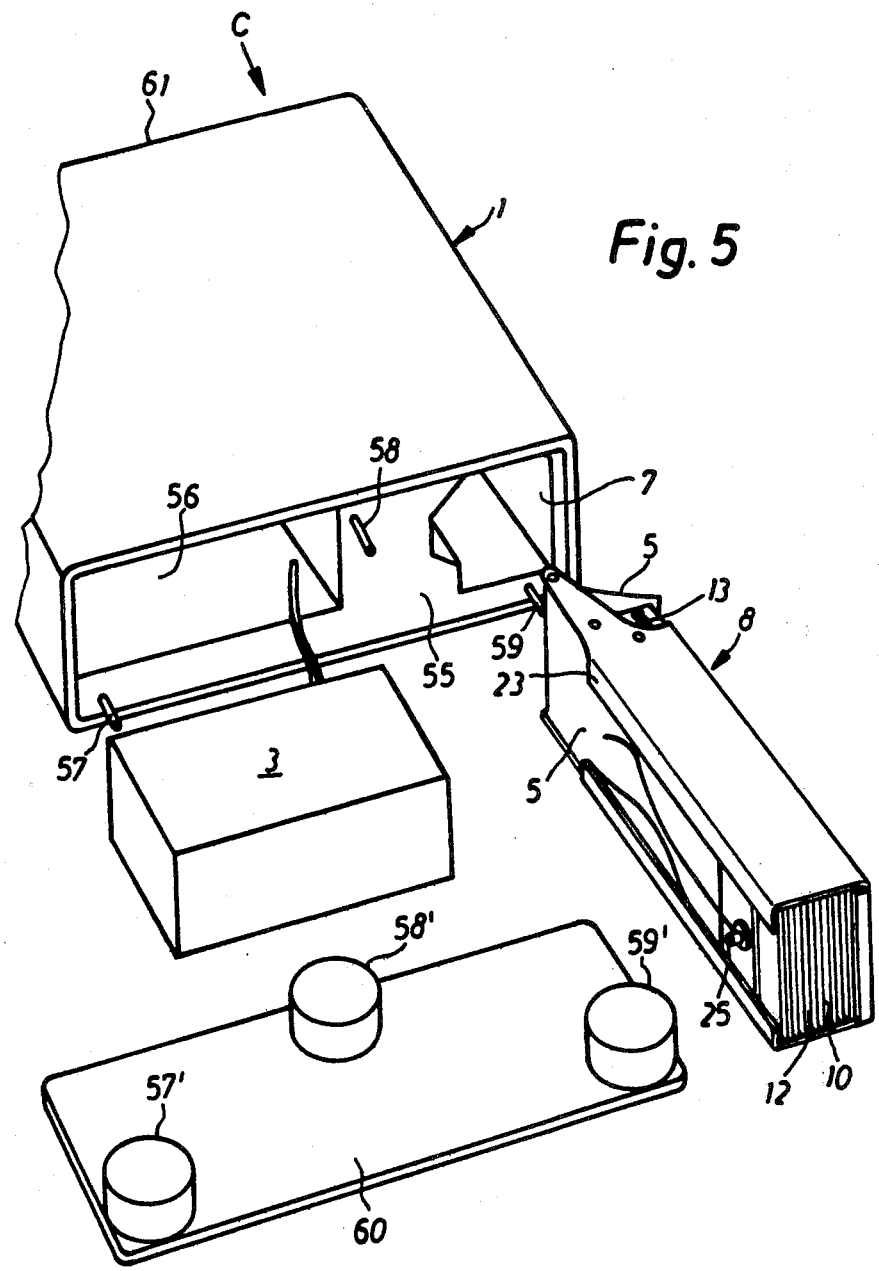
FIG. 5 is a perspective view of an electrocardiograph with parts removed therefrom, and whereby there is shown the cassette in a position in accordance with FIGS. 3 and 4.

This removed state of the battery unit 3 as well as the removed state of the tape cassette 8 is shown in FIG. 5. The face wall 55 with the container means 7 for the casket and a container means 56 for the battery unit 3 is provided with three electrode pins 57, 58, 59 cooperating with corresponding set down electrodes 57', 58', 59', which can be set upon the human thorax and are mounted on top of a cover plate 60 (FIG. 5; not shown in FIG. 1).

In FIG. 6 there is shown a view of the complete electrocardiograph in its ready to use state, whereby the control panel 80 is facing the surgeon. On the left hand side of the Figure there is to be seen the paper web 5 depicting an electrocardiographic curve 81. (See also FIG. 1.) In the control panel there is formed a window 82 through which the paper web and the stylus 6 can be viewed by the operator. The knob 83 is to set the initial position of the stylus 6 and the knob 84 for controlling the amplification of the signal on the paper web. The light 85 indicates the state of the battery charge and by 86 there is provided the on-off power switch. The plug-in connections 87 are provided for connection with a remote control unit. These parts and functions of the unit are known and not further described.

In use, the apparatus is placed upon the thorax of the patient at the area of the heart, whereby panel 80 faces the operator and the cover plate 60 contacts the patient, as mentioned above.

Due to the space-saving construction of the paper supply portion comprising the cassette 8 and the container 7 the described electrocardiograph can be designed to have extremely small dimensions and a very light weight and is, therefore, due to these facts and also due to its capability to operate independently from a community power supply network quite suitable for an ambulant measurement of the performance of the heart.

The inventive device for supplying an imprinting apparatus has been described above in combination with an electrocardiograph.

It shall, however, be understood that this is only one of the various embodiments of the invention; thus the device is intended to be used in combination with other apparatuses providing records and also comprising a variety of arrangements and particulars of the recording tape or web.

Accordingly, there is shown in FIG. 7 a recording tape 101 stored in a spirally wound form.

Also, the recording tape is envisaged to be of varying material, depending upon the apparatus used.

Thus this tape can be a paper tape to record characters provided by a recording stylus discharging ink. The tape can be superimposed with a typewriter ribbon like tape, whereby a pressure exerting stylus is provided.

The tape may be provided with a superimposed wax layer or layer of soot, carbon black, whereby the stylus scratches the superimposed layer off to give a recording. There can be the electrically heated stylus generating a trace of a contrasting color of the accordingly prepared tape. The tape can be provided with a metallic covering layer, such as a zinc-cadmium layer. There also can be used a light-sensitive covering layer, the trace being generated by a light source.

Since many modifications, variations and changes in detail may be made to the described embodiments, it is intended that all matter contained in the foregoing description or shown in the accompanying drawings be interpreted as illustrative and not in a limiting sense.

What is claimed is:

1. A device for supplying recording paper tape to an imprinting apparatus comprising
   a cassette having a storage space therein for storage of a condensed supply of recording tape, the cassette being movable between an operating position and a refilling position;
   a driving roll positioned on the imprinting apparatus adjacent the cassette; and
   a non-driven pressure roll positioned at the front end of the cassette so as to contact the driving roll when the cassette is in its operating position to form a clamping gap between the two rolls through which the recording tape is received;
   the cassette being insertable into said imprinting apparatus as well as retractable from said imprinting apparatus and arranged to be completely removable therefrom.

2. The device of claim 1, characterized in that said recording tape means is stored in said container means in a folded, pleated form.

3. The device of claim 1, characterized in that said recording tape means is stored in said container means in a rolled form.

4. The device of claim 1, comprising further a spring means biassing said pressure roll in a direction towards said clamping gap.

5. The device of claim 1, characterized in that said recording tape means comprises a paper tape.

6. The device of claim 1, characterized in that said recording tape means comprises a plastic tape.

7. The device of claim 1, characterized in that said recording tape means comprises a carrier tape supporting a covering layer having a contrasting color.

8. The device of claim 1, characterized in that said recording tape means comprises a carrier tape supporting a metallic covering layer.

9. The device of claim 1, comprising further a guide roll arranged within said cassette, which guide roll deflects the leading portion of said recording tape means prior to its entry into said clamping gap.

10. The device of claim 9, wherein said guide roll is substantially in alignment with the tape portion drawn off from the accumulated stored tape means and said pressure roll is arranged beyond said guide roll and offset therefrom such as to produce a deflection of the drawn off tape portion prior to its entry into the clamping gap in an amount exceeding 90°.

11. The device of claim 1, wherein said imprinting apparatus is provided with a receiving means for said cassette, said receiving means having a C-like cross section and being arranged within said imprinting apparatus, said receiving means serving as support for said driving roll and its driving means and simultaneously forming a guiding means for said cassette.

12. The device of claim 11, wherein said cassette and said its receiving means is provided each with a portion of a locking means, said portions being engaged when said cassette is in its operating position.

13. The device of claim 12, wherein said receiving means is provided with at least one leaf spring means for holding down the recording tape means section to be inserted against a guide surface provided at the cassette.

* * * * *